United States Patent
Brown et al.

(12)

(10) Patent No.: US 6,426,405 B2
(45) Date of Patent: Jul. 30, 2002

(54) NEUROTRANSMITTER TRANSPORTER SC6

(75) Inventors: Anthony M Brown, Harston; Conrad Gerald Chapman, Orpington; Israel Simon Gloger, London; Joanne Rachel Evans, Old Harlow; William Cairns, Harlow; Hugh Jonathan Herdon, Saffron Walden, all of (GB)

(73) Assignee: SmithKline Beecham P.L.C., Brentford (GB)

( * ) Notice: Subject to any disclaimer, the term of this patent is extended or adjusted under 35 U.S.C. 154(b) by 0 days.

(21) Appl. No.: 09/795,232

(22) Filed: Feb. 28, 2001

Related U.S. Application Data

(62) Division of application No. 09/182,728, filed on Oct. 29, 1998.

(30) Foreign Application Priority Data

Aug. 28, 1998 (GB) .............................................. 9818890

(51) Int. Cl.$^7$ .............................................. C07K 14/00
(52) U.S. Cl. ...................................... 530/350; 530/351
(58) Field of Search ........................... 530/350; 435/7.1, 435/35, 69.1, 183

(56) References Cited

U.S. PATENT DOCUMENTS 5,919,653 A    7/1999  Albert et al.

FOREIGN PATENT DOCUMENTS

| WO | WO 90/06047 | 6/1990 |
| WO | WO 93/10228 | 5/1993 |
| WO | WO 97/45446 | 12/1997 |
| WO | WO 98/07854 | 2/1998 |

OTHER PUBLICATIONS

Liu et al. "Cloning and Expression of a Spinal Cord– and Brain–specific Glycine Transporter with Novel Structural Features", Journal of Biological Chemistry, vol. 268 (30), pp. 22802–22808 (1993).

Ponce et al. "Characterization of the 5' region of the rat brain glycine transporter GLYT2 gene: Identification of a novel isoform", Neuroscience Letters, vol. 242, pp. 25–28 (1998).

GenBank Accession No. L21672 (Dec. 31, 1993).

PIR Accession No. A48716 (Jun. 2, 1995).

Verma et al. "Gene therapy—promises, problems and prospects", Nature 389: 239–242 (1997).

Orkin et al. "Report and recommendations of the panel to assess the NIH investment in research on gene therapy", issued by the U.S. National Institute of Health (1995).

*Primary Examiner*—Elizabeth C. Kermmerer
*Assistant Examiner*—Sandra Wegert
(74) *Attorney, Agent, or Firm*—RatnerPrestia

(57) ABSTRACT

The SC6 polypeptides and polynucleotides and methods for producing such polypeptides by recombinant techniques are disclosed. Also disclosed are methods for utilizing SC6 polypeptides and polynucleotides in therapy, and diagnostic assays for such.

2 Claims, 2 Drawing Sheets

Time course of [$^3$H]- glycine uptake into HEK-293 cells transfected with SC6

NEUROTRANSMITTER TRANSPORTER SC6

This application is a Divisional of U.S. patent application Ser. No. 09/182,728 filed Oct. 29, 1998, the entire disclosure of which is expressly incorporated by reference herein.

FIELD OF THE INVENTION

This invention relates to newly identified polypeptides and polynucleotides encoding such polypeptides, to their use in therapy and in identifying compounds which may be agonists, antagonists and /or inhibitors which are potentially useful in therapy, and to production of such polypeptides and polynucleotides.

BACKGROUND OF THE INVENTION

The drug discovery process is currently undergoing a fundamental revolution as it embraces 'functional genomics', that is, high throughput genome- or gene-based biology. This approach as a means to identify genes and gene products as therapeutic targets is rapidly superceding earlier approaches based on 'positional cloning'. A phenotype, that is a biological function or genetic disease, would be identified and this would then be tracked back to the responsible gene, based on its genetic map position.

Functional genomics relies heavily on high-throughput DNA sequencing and the various tools of bioformatics to identify gene sequences of potential interest from the many molecular biology databases now available. There is a continuing need to identify and characterise further genes and their related polypeptides/proteins, as targets for drug discovery.

In the central and peripheral nervous system, reliable neurotransmission depends on rapid termination of transmitter action following postsynaptic activation. In some cases this is achieved by metabolism of the neurotransmitter, as in the case of acetycholine and neuropeptides. In many cases, however, including catecholamines, serotonin and some amino acids (e.g. GABA, glycine and glutamate), the neurotransmitter is efficiently removed into the presynaptic terminal or surrounding glial cells by neurotransmitter transporters, membrane-bound polypeptides located in the plasma membrane.

Recently, cDNAs encoding a number of Na/Cl-dependent neurotransmitter transporters (e.g. for serotonin, catecholamine, amino acid (glycine, GABA)) have been described. The general structure of this class of transporter is very similar, containing twelve potential transmembrane helices and an external loop with 3–4 glycosylation sites between transmembrane segments 3 and 4. In GABA and catecholamine transporter subfamilies, the amino acid sequence is about 60–80% identical to other members within a subfamily and about 40% identical to members between two subfamilies (Liu et al., Proc. Natl. Acad. Sci. USA, (1992), 89:6639–6643). Transporters of amino acids such as glycine share about 40–50% homology with all members of the neurotransmitter transporter superfamily. Two classes of glycine transporter, GlyT-1 and GlyT-2, have been identified (Liu et al, J. Biol. Chem. (1992),268, 22802–22808). Rat GlyT-2 has about 50% amino acid sequence identity with either human or rat GlyT-1.

Glycine is a major transmitter in the nervous system. Glycine can have both inhibitory and excitatory functions, which are mediated by two different types of receptor, each associated with a different class of glycine transporter. The excitatory function of glycine is mediated by "strychnine-insensitive" glycine receptors, which are part of the NMDA receptor complex which mediates some of the actions of glutamate, the major excitatory transmitter in the central nervous system. This type of glycine receptor is widely distributed throughout the brain, and is associated with the GlyT-1 transporter. Conversly, the inhibitory action of glycine is mediated by "strychnine-sensitive" glycine receptors. These receptors are found mainly in the spinal cord, brainstem and cerebellum, and are associated with the GlyT-2 transporter.

Modulation of neurotransmitter transport enables synaptic transmission to be increased or decreased by altering the levels of neurotransmitter in the synaptic cleft, and blockade of transport is an established approach to the treatment of psychiatric and neurological illness. Drugs which act by this mechanism include the tricyclic antidepressants, which act on monamine transporters in general, and the selective serotonin uptake inhibitors (SSRIs) (Lesch K P and Bengel D, CNS Drugs 4(1995), 302–322). A GABA transport inhibitor, tiagabine, has recently been identified as a potential therapy for epilepsy (Lesch K P and Bengel D, CNS Drugs 4(1995), 302–322. Compounds which modulate glycine transporter function would be expected to alter synaptic levels of glycine and thus affect receptor function. In the case of the GlyT-2 transporter, inhibition of transporter function would produce increased activation of strychnine-sensitive glycine receptors. In the spinal cord, activation of these receptors would be expected to reduce transmission of pain-related information, so inhibition of the GlyT-2 transporter could alleviate neuropathic or other pain sensation (e.g. Simpson R K et al, Neurochem. Res. (1996) 21, 1221–1226). In addition, activation of strychnine-sensitive glycine receptors can reduce muscle hyperactivity, which can be related to conditions such as myoclonus, epilepsy and spasticity (e.g. Simpson R K et al, J. Spinal Cord Med. (1996) 19, 215–224). Therefore, inhibition of the glycine transporter could alleviate spasticity or other muscle hyperactivity associated with epilepsy, stroke, head trauma, spinal cord injury, dystonia, multiple sclerosis amyotrophic lateral sclerosis, Huntington's Disease or Parkinson's Disease

SUMMARY OF THE INVENTION

Figure 1:
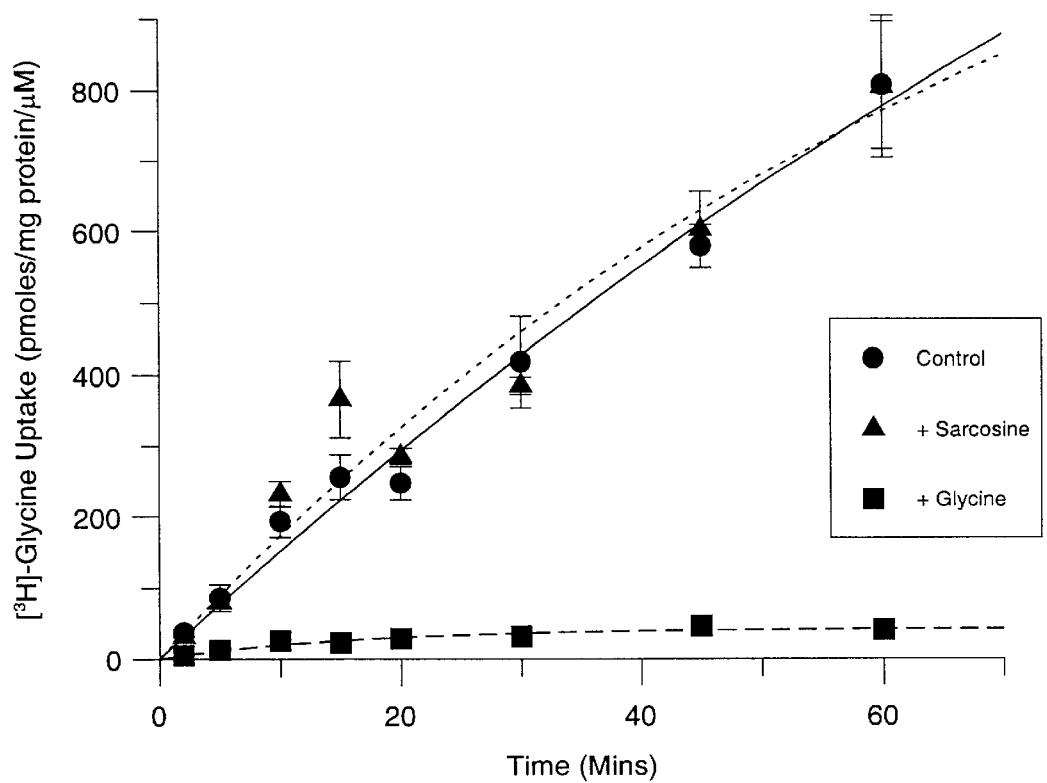
FIG. 1 is a chart showing the course of [$^3$H]-glycine uptake into HEK-293 cells transfected with SC6.

The present invention relates to SC6, in particular SC6 polypeptides and SC6 polynucleotides, recombinant materials and methods for their production. In another aspect, the invention relates to methods for using such polypeptides and polynucleotides, including the treatment of neuropathic pain, other pain, spasticity, myoclonus, epilepsy, stroke, head trauma, spinal cord injury, dystonia, multiple sclerosis, amyotrophic lateral sclerosis, Huntington's Disease or Parkinson's Disease, hereinafter referred to as "the Diseases", amongst others. In a further aspect, the invention relates to methods for identifying agonists and antagonists/inhibitors using the materials provided by the invention, and treating conditions associated with SC6 imbalance with the identified compounds. In a still further aspect, the invention relates to diagnostic assays for detecting diseases associated with inappropriate SC6 activity or levels.

DESCRIPTION OF THE INVENTION

In a first aspect, the present invention relates to SC6 polypeptides. Such peptides include isolated polypetides comprising an amino acid sequence which has at least 97% identity, preferably at least 99% identity, to that of SEQ ID NO:2 over the entire length of SEQ ID NO:2. Such polypeptides include those comprising the amino acid of SEQ ID NO:2.

Further peptides of the present invention include isolated polypeptides in which the amino acid sequence has at least 97% identity, preferably at least 99% identity, to the amino acid sequence of SEQ ID NO:2 over the entire length of SEQ ID NO:2. Such polypeptides include the polypeptide of SEQ ID NO:2.

Further peptides of the present invention include isolated polypeptides encoded by a polynucleotide comprising the sequence contained in SEQ ID NO:1.

Polypeptides of the present invention are believed to be members of the Neurotransmitter transporter family of polypeptides. They are therefore of interest because of the established, proven history of neurotransmitter transporters as therapeutic targets for the treatment of neurological or psychiatric diseases. In particular, glycine transporters would be expected to modulate activation of glycine receptors by glycine, and there is evidence that strychnine-sensitive glycine receptors can regulate transmission of pain information and modulate muscle activity. Therefore, a therapeutic target for treatment of diseases associated with altered muscle activity or pain transmission could be provided by a polypeptide which has the properties of a glycine transporter, in particular of the GlyT-2 type which is associated with strychnine-sensitive glycine receptors . . . These properties are hereinafter referred to as "SC6 activity" or "SC6 polypeptide activity" or "biological activity of SC6". Also included amongst these activities are antigenic and immunogenic activities of said SC6 polypeptides, in particular the antigenic and immunogenic activities of the polypeptide of SEQ ID NO:2. Preferably, a polypeptide of the present invention exhibits at least one biological activity of SC6.

The polypeptides of the present invention may be in the form of the "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to SC6 polynucleotides. Such polynucleotides include isolated polynucleotides comprising a nucleotide sequence encoding a polypeptide which has at least 97% identity, to the amino acid sequence of SEQ ID NO:2, over the entire length of SEQ ID NO:2. In this regard, polypeptides which have at least 99% identity are highly preferred. Such polynucleotides include a polynucleotide comprising the nucleotide sequence contained in SEQ ID NO:1 encoding the polypeptide of SEQ ID NO:2.

Further polynucleotides of the present invention include isolated polynucleotides comprising a nucleotide sequence that has at least 90% identity, preferably at least 95% identity, to a nucleotide sequence encoding a polypeptide of SEQ ID NO:2, over the entire coding region. In this regard, polynucleotides which have at least 97% identity are highly preferred, whilst those with at least 98–99% identity are more highly preferred, and those with at least 99% identity are most highly preferred.

Further polynucleotides of the present invention include isolated polynucleotides comprising a nucleotide sequence which has at least 90% identity, preferably at least 95% identity, to SEQ ID NO:1 over the entire length of SEQ ID NO:1. In this regard, polynucleotides which have at least 97% identity are highly preferred, whilst those with at least 98–99% identiy are more highly preferred, and those with at least 99% identity are most highly preferred. Such polynucleotides include a polynucleotide comprising the polynucleotide of SEQ ID NO:1 as well as the polynucleotide of SEQ ID NO:1.

The invention also provides polynucleotides which are complementary to all the above described polynucleotides.

The nucleotide sequence of SEQ ID NO:1 shows homology with Rat GlyT-2 glycine transporter (Q. R. Liu et al, J. Biol. Chem. (1993) 268: 22802–22808) (GenBank L21672). The nucleotide sequence of SEQ ID NO:1 is a cDNA sequence and comprises a polypeptide encoding sequence (nucleotide 256 to 2649) encoding a polypeptide of 797 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The polypeptide of the SEQ ID NO:2 is structurally related to other proteins of the Neurotransmitter transporter family, having homology and/or structural similarity with Rat GlyT-2 glycine transporter (Q. R. Liu et al, J. Biol. Chem. (1993) 268: 22802–22808) (PIR A48716).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one SC6 activity. Polynucleotides of the present invention may be obtained, using standard cloning and screening techniques, from a cDNA library derived from mRNA in cells of human spinal cord, using the expressed sequence tag (EST) analysis (Adams, M. D., et al. *Science* (1991) 252:1651–1656; Adams, M. D. et al., *Nature,* (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself; or the coding sequence for the mature polypeptide in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2 and in which several, for instance from 5 to 10, 1 to 5, 1 to 3, 1 to 2 or 1, amino acid residues are substituted, deleted or added, in any combination.

Polynucleotides which are identical or sufficiently identical to a nucleotide sequence contained in SEQ ID NO:1, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1. Typically these nucleotide sequences are 70% identical, preferably 80% identical, more preferably 90% identical, most preferably 95% identical to that of the referent. The probes or primers will generally comprise at least 15 nucleotides, preferably, at least 30 nucleotides and may have at least 50 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process which comprises the steps of screening an appropriate library under stringent hybridization conditions with a labeled probe having the sequence of SEQ ID NO:1 or a fragment thereof; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at about 65° C. Thus the present invention also includes polynucleotides obtainable by screening an appropriate library under stingent hybridization conditions with a labeled probe having the sequence of SEQ ID NO:1 or a fragment thereof.

The skilled artisan will appreciate that, in many cases, an isolated cDNA sequence will be incomplete, in that the region coding for the polypeptide is short at the 5' end of the cDNA. This is a consequence of reverse transcriptase, an enzyme with inherently low 'processivity' (a measure of the ability of the enzyme to remain attached to the template during the polymerisation reaction), failing to complete a DNA copy of the mRNA template during 1st strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analysed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as Streptococci, Staphylococci, *E. coli,* Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and or purification.

This invention also relates to the use of polynucleotides of the present invention as diagnostic reagents. Detection of a mutated form of the gene characterised by the polynucleotide of SEQ ID NO:1 which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled SC6 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (ee, e.g., Myers et al., *Science* (1985) 230:1242). Sequence changes at specific locations may also be revealed by nuclease protection assays, such as RNase and S1 protection or the chemical cleavage method (see Cotton et al., *Proc Natl Acad Sci USA* (1985) 85:4397–4401). In another embodiment, an array of oligonucleotides probes comprising SC6 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, Vol 274, pp 610–613 (1996)).

The diagnostic assays offer a process for diagnosing or determining a susceptibility to the Diseases through detection of mutation in the SC6 gene by the methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagnostic kit which comprises:

(a) a polynucleotide of the present invention, preferably the nucleotide sequence of SEQ ID NO: 1, or a fragment thereof;

(b) a nucleotide sequence complementary to that of (a);

(c) a polypeptide of the present invention, preferably the polypeptide of SEQ ID NO:2 or a fragment thereof; or (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or suspectability to a disease, particularly neuropathic pain, other pain, spasticity, myoclonus, epilepsy, stroke, head trauma, spinal cord injury, dystonia, multiple sclerosis, amyotrophic lateral sclerosis, Huntington's Disease or Parkinson's Disease, amongst others.

The nucleotide sequences of the present invention are also valuable for chromosomal localisation. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

The nucleotide sequences of the present invention are also valuable for tissue localisation. Such techniques allow the determination of expression patterns of the human SC6 polypeptides in tissues by detection of the mRNAs that encode them. These techniques include in situ hybridization techniques and nucleotide amplification techniques, for example PCR. Such techniques are well known in the art. Results from these studies provide an indication of the normal functions of the polypeptides in the organism. In addition, comparative studies of the normal expression pattern of human SC6 mRNAs with that of mRNAs encoded by a human SC6 gene provide valuable insights into the role of mutant human SC6 polypeptides, or that of inappropriate expression of normal human SC6 polypeptides, in disease. Such inappropriate expression may be of a temporal, spatial or simply quantitative nature.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

Antibodies against polypeptides of the present invention may also be employed to treat the Diseases, amongst others.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Another aspect of the invention relates to a method for inducing an immunological response in a mammal which comprises inoculating the mammal with a polypeptide of the present invention, adequate to produce antibody and/or T cell immune response to protect said animal from the Diseases hereinbefore mentioned, amongst others. Yet another aspect of the invention relates to a method of inducing immunological response in a mammal which comprises, delivering a polypeptide of the present invention via a vector directing expression of the polynucleotide and coding for the polypeptide in vivo in order to induce such an immunological response to produce antibody to protect said animal from diseases.

A further aspect of the invention relates to an immunological/vaccine formulation (composition) which, when introduced into a mammalian host, induces an immunological response in that mammal to a polypeptide of the present invention wherein the composition comprises a polypeptide or polynucleotide of the present invention. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention are responsible for one or more biological functions, including one or more disease states, in particular the Diseases hereinbefore mentioned. It is therefore desirous to devise screening methods to identify compounds which stimulate or which inhibit the function of the polypeptide. Accordingly, in a further aspect, the present invention provides for a method of screening compounds to identify those which stimulate or which inhibit the function of the polypeptide. In general, agonists or antagonists may be employed for therapeutic and prophylactic purposes for such Diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of the polypeptide; or may be structural or functional mimetics thereof (see Coligan et al., *Current Protocols in Immunology* 1(2):Chapter 5 (1991)).

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Constitutively active polypeptides may be employed in screening methods for inverse agonists or inhibitors, in the absence of an agonist or inhibitor, by testing whether the candidate compound results in inhibition of activation of the polypeptide. Further, the screening methods may simply comprise the steps of mixing a candidate compound with a solution containing a polypeptide of the present invention, to form a mixture, measuring SC6 activity in the mixture, and comparing the SC6 activity of the mixture to a standard. Fusion proteins, such as those made from Fc portion and SC6 polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

As an example, activity of a neurotransmitter transporter may be determined in cells in culture through use of a radiolabelled substrate. After exposure of the cells to the substrate (added to the culture medium) for a defined length of time, the cells are washed, their contents extracted by treatment with acid or alkali and the cellular accumulation of radiolabel determined by scintillation spectrometry. In this way, maximal activity, substrate concentration required for half maximal activity (Km) and the potency of competing agents (e.g. small molecules) can be determined by established methods (see e.g. Clark J A and Amara S, Mol. Pharmacol. 46 (1994), 550–557). In order to determine whether competing agents actually inhibit transporter function, it is necessary to distinguish between agents which block the activity of the transporter and agents which reduce radiolabelled substrate accumulation in the cells by acting in themselves as substrates for the transporter. This can be assessed by first preloading the cells with radiolabelled substrate in the absence of any competing agent. Measurements can then be made of the subsequent efflux of radiolabelled substrate from the cells under conditions which favour "reverse" activity of the transporter (e.g. low extracellular concentrations of Na+ and Cl− ions). An agent which acts as a substrate for the transporter should increase this efflux, whereas an agent which is a true inhibitor of transporter function should decrease it (see e.g. Chen N et al, J. Neurochem. (1998) 71, 653–665).

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The polypeptide may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide which compete with the binding of the polypeptide to its receptors, if any. Standard methods for conducting such assays are well understood in the art.

Examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Thus, in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:

(a) a polypeptide of the present invention;
(b) a recombinant cell expressing a polypeptide of the present invention;
(c) a cell membrane expressing a polypeptide of the present invention; or
(d) antibody to a polypeptide of the present invention;
which polypeptide is preferably that of SEQ ID NO:2.

It will be appreciated that in any such kit, (a), (b), (c) or (d) may comprise a substantial component.

It will be readily appreciated by the skilled artisan that a polypeptide of the present invention may also be used in a method for the structure-based design of an agonist, antagonist or inhibitor of the polypeptide, by:

(a) determining in the first instance the three-dimensional structure of the polypeptide;
(b) deducing the three-dimensional structure for the likely reactive or binding site(s) of an agonist, antagonist or inhibitor;
(c) synthesing candidate compounds that are predicted to bind to or react with the deduced binding or reactive site; and
(d) testing whether the candidate compounds are indeed agonists, antagonists or inhibitors.

It will be further appreciated that this will normally be an iterative process.

In a further aspect, the present invention provides methods of treating abnormal conditions such as, for instance, neuropathic pain, other pain, spasticity, myoclonus, epilepsy, stroke, head trauma, spinal cord injury, dystonia, multiple sclerosis, amyotrophic lateral sclerosis, Huntington's Disease or Parkinson's Disease, related to either an excess of, or an under-expression of, SC6 polypeptide activity.

If the activity of the polypeptide is in excess, several approaches are available. One approach comprises administering to a subject in need thereof an inhibitor compound (antagonist) as hereinabove described, optionally in combination with a pharmaceutically acceptable carrier, in an amount effective to inhibit the function of the polypeptide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide may be administered. Typical examples of such competitors include fragments of the SC6 polypeptide.

In still another approach, expression of the gene encoding endogenous SC6 polypeptide can be inhibited using expression blocking techniques. Known such techniques involve the use of antisense sequences, either internally generated or externally administered (see, for example, O'Connor, J

*Neurochem* (1991) 56:560 in Oligodeoxynucleotides as Antisense Inhibitors of Gene Expression, CRC Press, Boca Raton, Fla. (1988)). Alternatively, oligonucleotides which form triple helices ("triplexes") with the gene can be supplied (see, for example, Lee et al., *Nucleic Acids Res* (1979) 6:3073; Cooney et al., *Science* (1988) 241:456; Dervan et al., *Science* (1991) 251:1360). These oligomers can be administered per se or the relevant oligomers can be expressed in vivo. Synthetic antisense or triplex oligonucleotides may comprise modified bases or modified backbones. Examples of the latter include methylphosphonate, phosphorothioate or peptide nucleic acid backbones. Such backbones are incorporated in the antisense or triplex oligonucleotide in order to provide protection from degradation by nucleases and are well known in the art. Antisense and triplex molecules synthesised with these or other modified backbones also form part of the present invention.

In addition, expression of the human SC6 polypeptide may be prevented by using ribozymes specific to the human SC6 mRNA sequence. Ribozymes are catalytically active RNAs that can be natural or synthetic (see for example Usman, N, et al., Curr. Opin. Struct. Biol (1996) 6(4), 527–33.) Synthetic ribozymes can be designed to specifically cleave human SC6 mRNAs at selected positions thereby preventing translation of the human SC6 mRNAs into functional polypeptide. Ribozymes may be synthesised with a natural ribose phosphate backbone and natural bases, as normally found in RNA molecules. Alternatively the ribosymes may be synthesised with non-natural backbones to provide protection from ribonuclease degradation, for example, 2'-O-methyl RNA, and may contain modified bases.

For treating abnormal conditions related to an underexpression of SC6 and its activity, several approaches are also available. One approach comprises administering to a subject a therapeutically effective amount of a compound which activates a polypeptide of the present invention, i.e., an agonist as described above, in combination with a pharmaceutically acceptable carrier, to thereby alleviate the abnormal condition. Alternatively, gene therapy may be employed to effect the endogenous production of SC6 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, *Gene Therapy and other Molecular Genetic-based Therapeutic Approaches,* (and references cited therein) in Human Molecular Genetics, T Strachan and A P Read, BIOS Scientific Publishers Ltd (1996). Another approach is to administer a therapeutic amount of a polypeptide of the present invention in combination with a suitable pharmaceutical carrier.

In a further aspect, the present invention provides for pharmaceutical compositions comprising a therapeutically effective amount of a polypeptide, such as the soluble form of a polypeptide of the present invention, agonist/antagonist peptide or small molecule compound, in combination with a pharmaceutically acceptable carrier or excipient. Such carriers include, but are not limited to, saline, buffered saline, dextrose, water, glycerol, ethanol, and combinations thereof.

The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

The dosage range required depends on the choice of peptide or other compounds of the present invention, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Polynucleotide and polypeptide sequences form a valuable information resource with which to identify further sequences of similar homology. This is most easily facilitated by storing the sequence in a computer readable medium and then using the stored data to search a sequence database using well known searching tools, such as those in the GCG and Lasergene software packages. Accordingly, in a further aspect, the present invention provides for a computer readable medium having stored thereon a polynucleotide comprising the sequence of SEQ ID NO:1 and/or a polypeptide sequence encoded thereby.

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, PROTEINS—STRUCTURE AND MOLECULAR PROPERTIES, 2nd Ed., T. E. Creighton, W. H. Freeman and Company, New York, 1993; Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Post-translational Modifications and Aging", *Ann NY Acad Sci* (1992) 663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.,* 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Preferred parameters for polypeptide sequence comparison include the following:

1) Algorithm: Needleman and Wunsch, *J. Mol Biol.* 48: 443–453 (1970)

Comparison matrix: BLOSSUM62 from Hentikoff and Hentikoff, Proc. Natl. Acad. Sci. USA. 89:10915–10919 (1992)

Gap Penalty: 12
Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:

1) Algorithm: Needleman and Wunsch, J. Mol Biol. 48: 443–453 (1970)
Comparison matrix: matches=+10, mismatch=0
Gap Penalty: 50
Gap Length Penalty: 3

Available as: The "gap" program from Genetics Computer Group, Madison Wis. These are the default parameters for nucleic acid comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity (divided by 100) and subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity (divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

"Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared as hereinbefore described. Falling within this generic term are the terms "ortholog", meaning a polynucleotide or polypeptide that is the functional equivalent of a polynucleotide or polypeptide in another species, and "paralog" meaning a functionally similar sequence when considered within the same species.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

All publications, including but not limited to patents and patent applications, cited in this specification are herein incorporated by reference as if each individual publication were specifically and individually indicated to be incorporated by reference herein as though fully set forth.

EXAMPLE 1

Cloning

The nucleotide sequence 256 to 2649 of SEQ ID NO:1 was obtained by PCR using gene specific primers, SEQ ID NO:3 (5' primer) and SEQ ID NO:4 (3' primer), to amplify up the full length clone. The template used for this PCR was 1st strand cDNA, produced using AMV Reverse transcriptase and an oligo(dT) primer, on a 500 ng poly A+ Spinal Cord RNA (Clontech). The reverse transcriptase reaction was carried out using the Promega RT system. Reaction conditions were: 1×RT buffer, 1 mM dNTPs, 5 mM $Mg^{2+}$, 10 units RNasin, 7.5 units AMV reverse transcriptase, 0.25 ug oligo(dT)15 Primer, 500 ng RNA template. The oligo(dT) primer was added to the polyA+ RNA and the reaction incubated for 70° C. for 10 minutes, then placed on ice. The reaction was then incubated at 42° C. for 60 minutes, followed by 99° C. for 5 minutes and then onto ice. The reaction product was diluted 1:10 for use in the PCR reaction.

The PCR reaction was carried out in 50 ul volume: 1×Klentaq Buffer, 0.2 mM dNTPs, 100 nM 5'Primer (SEQ ID NO:3), 100 nM 3'Primer (SEQ ID NO:4), 5 ul Spinal cord 1st strand cDNA (above), 1× KlenTaq polymerase mix. Cycling was at 95° C. for 2 minutes followed by 35 cycles of: 95° C. for 30 sec; 62° C. for 30 sec and 68° C. for 4 min. This was followed by a 10 minute hold at 68° C., then to 4° C.

Also included in Seq ID NO:1 are 5' and 3' untranslated (UTR) sequences. These were obtained separately. The 5'UTR (nucleotide 1 to 255) was obtained from an independent PCR on a Marathon cerebellum cDNA template, using 5'RACE PCR conditions (as recommended by the manufacturer) with gene specific primers, SEQ ID NO:5 (first-round primer) and SEQ ID NO:6 (nesting primer), together with Marathon adapter primers. The 3' UTR (nucleotide 2650 to 2863) was obtained by sequencing of Image clone No:745336; Soares NHT normalised human testis.

EXAMPLE 2

Mammalian Cell Expression

The transporter of the present invention was expressed transiently in human embryonic kidney 293 (HEK-293) cells. To maximise expression, typically 5' and 3' untranslated regions (UTRs) are removed from the transporter cDNA prior to transfection. Cells were transiently transfected using lipofectin. 24–48 hours after transfection, glycine transport activity was assayed as described in Example 2.

EXAMPLE 3

Glycine Uptake Assay

Suspensions of cells transiently transfected as described in Example 1 were pipetted into polylysine-colated 96 well plates (50,000 cells per well). 4–24 hours later, the wells were washed with standard Krebs/HEPES buffer (KHB) at 37° C. After addition of further KHB to the wells, the plates were incubated at 37° C. for 10 min. KHB containing appropriate concentrations of a potential inhibitor was then added to the wells, together with 1 μM [3H]-glycine. After incubation at 37° C. for 2–60 min, the wells were washed with ice-cold KHB. The cells were then solubilised in NaOH, and the amount of radioactivity present determined using a scintillation counter.

An example of the time course of [3H]-glycine uptake in cells transfected with SC6 is shown in FIG. 1. This [3H]-glycine uptake is almost totally blocked by inclusion of non-radioactive glycine (1 mM) in the assay, but is not significantly affected by sarcosine (1 mM). This lack of effect of sarcosine (a blocker of uptake via the GlyT-1 transporter), together with the fact that all assays were performed in the presence of alanine (5 mM) to block uptake via neutral amino acid transporter component of uptake, indicates that the [3H]-glycine uptake was mediated by the GlyT-2 transporter (Liu Q R et al, J. Biol. Chem. (1993) 268, 220802–22808).

Figure 2:
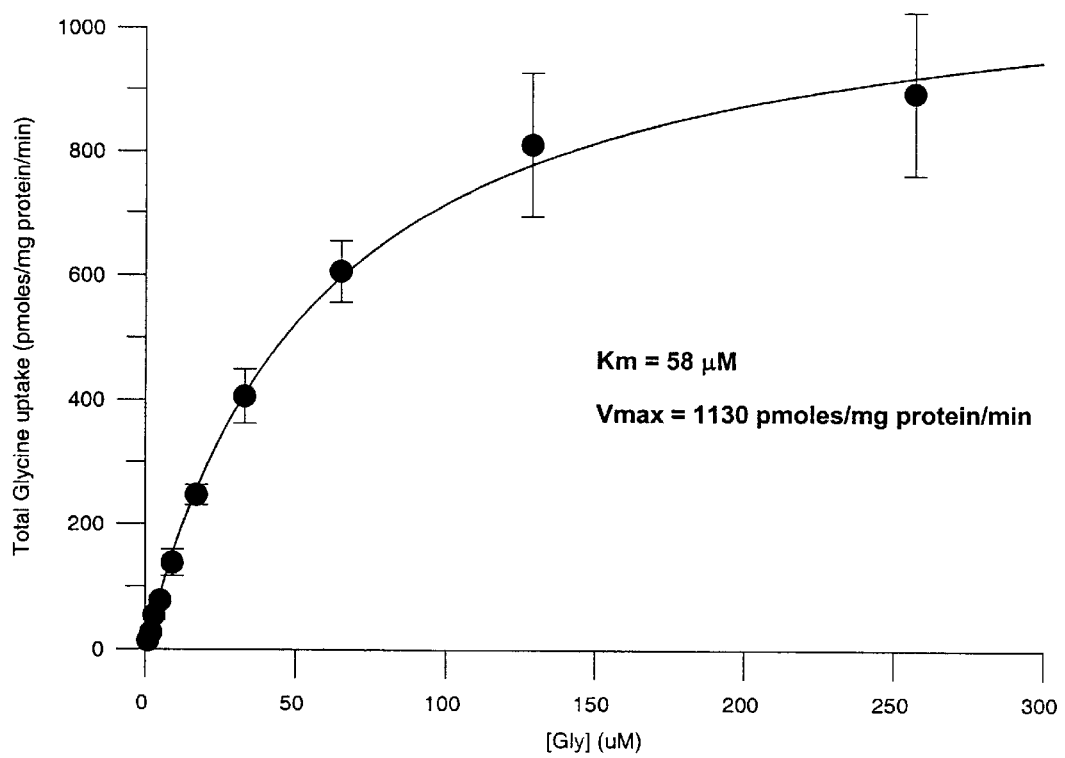
FIG. 2 is a chart showing the total glycine uptake at a range of glycine concentrations in HEK-293 cells transfected with SC6.

[3H]-glycine uptake as a function of the total concentration of glycine added to cells transfected with SC6 is shown in FIG. 2. The results indicate a Km value of 58 nM and a Vmax value of 1130 pmoles/mg protein/min.

SEQUENCE INFORMATION
SEQ ID NO:1
CCCTCCCGCTGGAGTGACAACTGGCCAGCATACTCTAGGCTGTTGTCCCT

TTAAAACTTGAATCCAAGGGGTAATGATTTATCAAACTTGTATTATCAA

GAAAATGTCAAACCAAGGGCACCTTGCTTTGCACTGACGCAAACCCGGCC

TTTCCCAAGGAGATATAGAAAGCGCCTCTCCTGCCTGAGCCAAACCCAGT

CTTGTCAATAGCGGGTTTCACCCTCCACTAGTTCAGTCTGTTGCCTGTGT

CAGACATGGATTGCAGTGCTCCCAAGGAAATGAATAAACTGCCAGCCAAC

AGCCCGGAGGCGGCGGCGGCGCAGGGCCACCCGGATGGCCCATGCGCTCC

-continued
CAGGACGAGCCCGGAGCAGGAGCTTCCCGCGGCCGCCGCCCCGCCGCCGC

CACGTGTGCCCAGGTCCGCTTCCACCGGCGCCCAAACTTTCCAGTCAGCG

GACGCGCGAGCCTGCGAGGCTGAGCGGCCAGGAGTGGGGTCTTGCAAACT

CAGTAGCCCGCGGGCGCAGGCGGCCTCTGCAGCTCTGCGGGACTTGAGAG

AGGCGCAAGGCGCGCAGGCCTCGCCCCCTCCCGGGAGCTCCGGGCCCGGC

AACGCGCTGCACTGTAAGATCCCTTCTCTGCGAGGCCCGGAGGGGGATGC

GAACGTGAGTGTGGGCAAGGGCACCCTGGAGCGGAACAATACCCCTGTTG

TGGGCTGGGTGAACATGAGCCAGAGCACCGTGGTGCTGGGCACGGATGGA

ATCACGTCCGTGCTCCCGGGCAGCGTGGCCACCGTTGCCACCCAGGAGGA

CGAGCGAGGGGATGAGAATAAGGCCCGAGGGAACTGGTCCAGCAAACTGG

ACTTCATCCTGTCCATGGTGGGGTACGCAGTGGGGCTGGGCAATGTCTGG

AGGTTTCCCTACCTGGCCTTCCAGAACGGGGGAGGTGCTTTCCTCATCCC

TTACCTGATGATGCTGGCTCTGGCTGGATTACCCATCTTCTTCTTGGAGG

TGTCGCTGGGCCAGTTTGCCAGCCAGGGACCAGTGTCTGTGTGGAAGGCC

ATCCCAGCTCTACAAGGCTGTGGCATCGCGATGCTGATCATCTCTGTCCT

AATAGCCATATACTACAATGTGATTATTTGCTATACACTTTTCTACCTGT

TTGCCTCCTTTGTGTCTGTACTACCCTGGGGCTCCTGCAACAACCCTTGG

AATACGCCAGAATGCAAAGATAAAACCAAACTTTTATTAGATTCCTGTGT

TATCAGTGACCATCCCAAAATACAGATCAAGAACTCGACTTTCTGCATGA

CCGCTTATCCCAACGTGACAATGGTTAATTTCACCAGCCAGGCCAATAAG

ACATTTGTCAGTGGAAGTGAAGAGTACTTCAAGTACTTTGTGCTGAAGAT

TTCTGCAGGGATTGAATATCCTGGCGAGATCAGGTGGCCACTAGCTCTCT

GCCTCTTCCTGGCTTGGGTCATTGTGTATGCATCGTTGGCTAAAGGAATC

AAGACTTCAGGAAAAGTGGTGTACTTCACGGCCACGTTCCCGTATGTCGT

ACTCGTGATCCTCCTCATCCGAGGAGTCACCCTGCCTGGAGCTGGAGCTG

GGATCTGGTACTTCATCACACCCAAGTGGGAGAAACTCACGAATGCCACG

GTGTGGAAAGATGCTGCCACTCAGATTTTCTTCTCTTTATCTGCTGCATG

GGGAGGCCTGATCACTCTCTCTTCTTACAACAAATTCCACAACAACTGCT

ACAGGGACACTCTAATTGTCACCTGCACCAACAGTGCCACAAGCATCTTT

GCCGGCTTCGTCATCTTCTCCGTTATCGGCTTCATGGCCAATGAACGCAA

AGTCAACATTGAGAATGTGGCAGACCAAGGGCCAGGCATTGCATTTGTGG

TTTACCCGGAAGCCTTAACCAGGCTGCCTCTCTCTCCGTTCTGGCCCATC

ATCTTTTTCCTGATGCTCCTCACTCTTGGACTTGACACTATGTTTGCCAC

CATCGAGACCATAGTGACCTCCATCTCAGACGAGTTTCCCAAGTACCTAC

GCACACACAAGCCAGTGTTTACTCTGGGCTGCTGCATTTGTTTCTTCATC

ATGGGTTTTCCAATGATCACTCAGGGTGGAATTTACATGTTTCAGCTTGT

GGACACCTATGCTGCCTCCTATGCCCTTGTCATCATTGCCATTTTTGAGC

TCGTGGGGATCTCTTATGTGTATGGCTTGCAAAGATTCTGTGAAGATATA

GAGATGATGATTGGATTCCAGCCTAACATCTTCTGGAAAGTCTGCTGGGC

ATTTGTAACCCCAACCATTTTAACCTTTATCCTTTGCTTCAGCTTTTACC

-continued

AGTGGGAGCCCATGACCTATGGCTCTTACCGCTATCCTAACTGGTCCATG

GTGCTCGGATGGCTAATGCTCGCCTGTTCCGTCATCTGGATCCCAATTAT

GTTTGTGATAAAAATGCATCTGGCCCCTGGAAGATTTATTGAGAGGCTGA

AGTTGGCGTGCTCGCCACAGCCGGACTGGGGCCCATTCTTAGCTCAACAC

CGCGGGGAGCGTTACAAGAACATGATCGACCCCTTGGGAACCTCTTCCTT

GGGACTCAAACTGCCAGTGAAGGATTTGGAACTGGGCACTCAGTGCTAGT

CCAGTGGTGTGGGATGGTCCAGACTTGATCCTGTTTTTCCTCTCTGCCTC

CTCCTAATGTTTTCCATAGCTCTCCTCCCATTTTTCTTCATCTTTCTTCC

TACATCTTGGTTCACATCCACGCATGAGAGTGATTATGTAGAAAAGTAGG

CATAGTGTCGCATGCTGCAGTAAAGAGCTACATAGACCACCTGAAAAAAA

AAAAAAAAAAAAA

SEQ ID NO:2
MDCSAPKEMNKLPANSPEAAAAQGHPDGPCAPRTSPEQELPAAAAPPPPR

VPRSASTGAQTFQSADARACEAERPGVGSCKLSSPRAQAASAALRDLREA

QGAQASPPPGSSGPGNALHCKIPSLRGPEGDANVSVGKGTLERNNTPVVG

WVNMSQSTVVLGTDGITSVLPGSVATVATQEDERGDENKARGNWSSKLDF

ILSMVGYAVGLGNVWRFPYLAFQNGGGAFLIPYLMMLALAGLPIFFLEVS

LGQFASQGPVSVWKAIPALQGCGIAMLIISVLIAIYYNVIICYTLFYLFA

SFVSVLPWGSCNNPWNTPECKDKTKLLLDSCVISDHPKIQIKNSTFCMTA

YPNVTMVNFTSQANKTFVSGSEEYFKYFVLKISAGIEYPGEIRWPLALCL

FLAWVIVYASLAKGIKTSGKVVYFTATFPYVVLVILLIRGVTLPGAGAGI

-continued

WYFITPKWEKLTNATVWKDAATQIFFSLSAAWGGLITLSSYNKFHNNCYR

DTLIVTCTNSATSIFAGFVIFSVIGFMANERKVNIENVADQGPGIAFVVY

PEALTRLPLSPFWAIIFFLMLLTLGLDTMFATIETIVTSISDEFPKYLRT

HKPVFTLGCCICFFIMGFPMITQGGIYMFQLVDTYAASYALVIIAIFELV

GISYVYGLQRFCEDIEMMIGFQPNIFWKVCWAFVTPTILTFILCFSFYQW

EPMTYGSYRYPNWSMVLGWLMLACSVIWIPIMFVTKMHLAPGRFIERLKL

ACSPQPDWGPFLAQHRGERYKNMIDPLGTSSLGLKLPVKDLELGTQC

SEQ ID NO:3
GCC ACC ATG GAT TGC AGT GCT CCC AAG GA

SEQ ID NO:4
GGA CTA GCA CTG AGT GCC CAG TTC C

SEQ ID NO:5
CTC TCA GTC CCA GAG CTG CAG

SEQ ID NO:6
GGC TAC TGA GTT TGC AAG AC

---

What is claimed is:

1. An isolated polypeptide comprising the amino acid sequence of SEQ ID NO:2.

2. An isolated polypeptide consisting of the amino acid sequence of SEQ ID NO:2.

* * * * *

SEQUENCE LISTING

<160> NUMBER OF SEQ ID NOS: 6

<210> SEQ ID NO 1
<211> LENGTH: 2863
<212> TYPE: DNA
<213> ORGANISM: HOMO SAPIENS

<400> SEQUENCE: 1

```
ccctcccgct ggagtgacaa ctggccagca tactctaggc tgttgtccct ttaaaacttg      60
aatccaaggg gtaatgatt tatcaaactt gtattatcaa gaaatgtca aaccaagggc     120 accttgcttt gcactgacgc aaacccggcc tttcccaagg agatatagaa agcgcctctc     180
ctgcctgagc caaacccagt cttgtcaata gcgggtttca ccctccacta gttcagtctg     240
ttgcctgtgt cagacatgga ttgcagtgct cccaaggaaa tgaataaact gccagccaac     300
agcccggagg cggcggcggc gcagggccac ccggatggcc catgcgctcc caggacgagc     360
ccggagcagg agcttcccgc ggccgccgcc ccgccgcgc cacgtgtgcc caggtccgct     420
tccaccggcg cccaaacttt ccagtcagcg gacgcgcgag cctgcgaggc tgagcggcca     480
ggagtggggt cttgcaaact cagtagcccg cgggcgcagg cggcctctgc agctctgcgg     540
gacttgagag aggcgcaagg cgcgcaggcc tcgcccctc ccgggagctc cgggcccggc     600
aacgcgctgc actgtaagat cccttctctg cgaggcccgg aggggatgc gaacgtgagt     660
```

```
gtgggcaagg gcaccctgga gcggaacaat acccctgttg tgggctgggt gaacatgagc    720
cagagcaccg tggtgctggg cacggatgga atcacgtccg tgctcccggg cagcgtggcc    780
accgttgcca cccaggagga cgagcgaggg gatgagaata aggcccgagg gaactggtcc    840
agcaaactgg acttcatcct gtccatggtg gggtacgcag tggggctggg caatgtctgg    900
aggtttccct acctggcctt ccagaacggg ggaggtgctt tcctcatccc ttacctgatg    960
atgctggctc tggctggatt acccatcttc ttcttggagg tgtcgctggg ccagtttgcc   1020
agccagggac cagtgtctgt gtggaaggcc atcccagctc tacaaggctg tggcatcgcg   1080
atgctgatca tctctgtcct aatagccata tactacaatg tgattatttg ctatacactt   1140
ttctacctgt ttgcctcctt tgtgtctgta ctaccctggg gctcctgcaa caaccccttgg   1200
```

-continued

```
<213> ORGANISM: HOMO SAPIENS

<400> SEQUENCE: 2

Met Asp Cys Ser Ala Pro Lys Glu Met Asn Lys Leu Pro Ala Asn Ser
 1               5                  10                  15

Pro Glu Ala Ala Ala Gln Gly His Pro Asp Gly Pro Cys Ala Pro
            20                  25                  30

Arg Thr Ser Pro Glu Gln Glu Leu Pro Ala Ala Ala Pro Pro Pro
        35                  40                  45

Pro Arg Val Pro Arg Ser Ala Ser Thr Gly Ala Gln Thr Phe Gln Ser
 50                  55                  60

Ala Asp Ala Arg Ala Cys Glu Ala Glu Arg Pro Gly Val Gly Ser Cys
 65                  70                  75                  80

Lys Leu Ser Ser Pro Arg Ala Gln Ala Ala Ser Ala Ala Leu Arg Asp
                 85                  90                  95

Leu Arg Glu Ala Gln Gly Ala Gln Ala Ser Pro Pro Gly Ser Ser
            100                 105                 110

Gly Pro Gly Asn Ala Leu His Cys Lys Ile Pro Ser Leu Arg Gly Pro
        115                 120                 125

Glu Gly Asp Ala Asn Val Ser Val Gly Lys Gly Thr Leu Glu Arg Asn
130                 135                 140

Asn Thr Pro Val Val Gly Trp Val Asn Met Ser Gln Ser Thr Val Val
145                 150                 155                 160

Leu Gly Thr Asp Gly Ile Thr Ser Val Leu Pro Gly Ser Val Ala Thr
                165                 170                 175

Val Ala Thr Gln Glu Asp Glu Arg Gly Asp Glu Asn Lys Ala Arg Gly
            180                 185                 190

Asn Trp Ser Ser Lys Leu Asp Phe Ile Leu Ser Met Val Gly Tyr Ala
        195                 200                 205

Val Gly Leu Gly Asn Val Trp Arg Phe Pro Tyr Leu Ala Phe Gln Asn
210                 215                 220

Gly Gly Gly Ala Phe Leu Ile Pro Tyr Leu Met Met Leu Ala Leu Ala
225                 230                 235                 240

Gly Leu Pro Ile Phe Phe Leu Glu Val Ser Leu Gly Gln Phe Ala Ser
                245                 250                 255

Gln Gly Pro Val Ser Val Trp Lys Ala Ile Pro Ala Leu Gln Gly Cys
            260                 265                 270

Gly Ile Ala Met Leu Ile Ile Ser Val Leu Ile Ala Ile Tyr Tyr Asn
        275                 280                 285

Val Ile Ile Cys Tyr Thr Leu Phe Tyr Leu Phe Ala Ser Phe Val Ser
290                 295                 300

Val Leu Pro Trp Gly Ser Cys Asn Asn Pro Trp Asn Thr Pro Glu Cys
305                 310                 315                 320

Lys Asp Lys Thr Lys Leu Leu Leu Asp Ser Cys Val Ile Ser Asp His
                325                 330                 335

Pro Lys Ile Gln Ile Lys Asn Ser Thr Phe Cys Met Thr Ala Tyr Pro
            340                 345                 350

Asn Val Thr Met Val Asn Phe Thr Ser Gln Ala Asn Lys Thr Phe Val
        355                 360                 365

Ser Gly Ser Glu Glu Tyr Phe Lys Tyr Phe Val Leu Lys Ile Ser Ala
370                 375                 380

Gly Ile Glu Tyr Pro Gly Glu Ile Arg Trp Pro Leu Ala Leu Cys Leu
385                 390                 395                 400
```

-continued

Phe Leu Ala Trp Val Ile Val Tyr Ala Ser Leu Ala Lys Gly Ile Lys
                405                 410                 415
Thr Ser Gly Lys Val Val Tyr Phe Thr Ala Thr Phe Pro Tyr Val Val
            420                 425                 430
Leu Val Ile Leu Leu Ile Arg Gly Val Thr Leu Pro Gly Ala Gly Ala
        435                 440                 445
Gly Ile Trp Tyr Phe Ile Thr Pro Lys Trp Glu Lys Leu Thr Asn Ala
450                 455                 460
Thr Val Trp Lys Asp Ala Ala Thr Gln Ile Phe Phe Ser Leu Ser Ala
465                 470                 475                 480
Ala Trp Gly Gly Leu Ile Thr Leu Ser Ser Tyr Asn Lys Phe His Asn
                485                 490                 495
Asn Cys Tyr Arg Asp Thr Leu Ile Val Thr Cys Thr Asn Ser Ala Thr
            500                 505                 510
Ser Ile Phe Ala Gly Phe Val Ile Phe Ser Val Ile Gly Phe Met Ala
        515                 520                 525
Asn Glu Arg Lys Val Asn Ile Glu Asn Val Ala Asp Gln Gly Pro Gly
530                 535                 540
Ile Ala Phe Val Val Tyr Pro Glu Ala Leu Thr Arg Leu Pro Leu Ser
545                 550                 555                 560
Pro Phe Trp Ala Ile Ile Phe Phe Leu Met Leu Leu Thr Leu Gly Leu
                565                 570                 575
Asp Thr Met Phe Ala Thr Ile Glu Thr Ile Val Thr Ser Ile Ser Asp
            580                 585                 590
Glu Phe Pro Lys Tyr Leu Arg Thr His Lys Pro Val Phe Thr Leu Gly
        595                 600                 605
Cys Cys Ile Cys Phe Phe Ile Met Gly Phe Pro Met Ile Thr Gln Gly
610                 615                 620
Gly Ile Tyr Met Phe Gln Leu Val Asp Thr Tyr Ala Ala Ser Tyr Ala
625                 630                 635                 640
Leu Val Ile Ile Ala Ile Phe Glu Leu Val Gly Ile Ser Tyr Val Tyr
                645                 650                 655
Gly Leu Gln Arg Phe Cys Glu Asp Ile Glu Met Met Ile Gly Phe Gln
            660                 665                 670
Pro Asn Ile Phe Trp Lys Val Cys Trp Ala Phe Val Thr Pro Thr Ile
        675                 680                 685
Leu Thr Phe Ile Leu Cys Phe Ser Phe Tyr Gln Trp Glu Pro Met Thr
690                 695                 700
Tyr Gly Ser Tyr Arg Tyr Pro Asn Trp Ser Met Val Leu Gly Trp Leu
705                 710                 715                 720
Met Leu Ala Cys Ser Val Ile Trp Ile Pro Ile Met Phe Val Ile Lys
                725                 730                 735
Met His Leu Ala Pro Gly Arg Phe Ile Glu Arg Leu Lys Leu Ala Cys
            740                 745                 750
Ser Pro Gln Pro Asp Trp Gly Pro Phe Leu Ala Gln His Arg Gly Glu
        755                 760                 765
Arg Tyr Lys Asn Met Ile Asp Pro Leu Gly Thr Ser Ser Leu Gly Leu
770                 775                 780
Lys Leu Pro Val Lys Asp Leu Glu Leu Gly Thr Gln Cys
785                 790                 795

<210> SEQ ID NO 3
<211> LENGTH: 29
<212> TYPE: DNA

```
<213> ORGANISM: HOMO SAPIENS

<400> SEQUENCE: 3
gccaccatgg attgcagtgc tcccaagga                              29

<210> SEQ ID NO 4
<211> LENGTH: 25
<212> TYPE: DNA
<213> ORGANISM: HOMO SAPIENS

<400> SEQUENCE: 4
ggactagcac tgagtgccca gttcc                                  25

<210> SEQ ID NO 5
<211> LENGTH: 24
<212> TYPE: DNA
<213> ORGANISM: HOMO SAPIENS

<400> SEQUENCE: 5
ctctcaagtc ccgcagagct gcag                                   24

<210> SEQ ID NO 6
<211> LENGTH: 20
<212> TYPE: DNA
<213> ORGANISM: HOMO SAPIENS

<400> SEQUENCE: 6
ggctactgag tttgcaagac                                        20
```